United States Patent
Zhou et al.

(10) Patent No.: US 8,995,608 B2
(45) Date of Patent: *Mar. 31, 2015

(54) COMPACT MICROBEAM RADIATION THERAPY SYSTEMS AND METHODS FOR CANCER TREATMENT AND RESEARCH

(71) Applicant: The University of North Carolina at Chapel Hill, Chapel Hill, NC (US)

(72) Inventors: Otto Z. Zhou, Chapel Hill, NC (US); Sha X. Chang, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/090,863

(22) Filed: Nov. 26, 2013

(65) Prior Publication Data

US 2014/0119496 A1    May 1, 2014

Related U.S. Application Data

(63) Continuation of application No. 12/688,425, filed on Jan. 15, 2010, now Pat. No. 8,600,003.

(51) Int. Cl.
*A61N 5/10* (2006.01)
*A61B 6/00* (2006.01)

(52) U.S. Cl.
CPC ............... *A61N 5/1069* (2013.01); *A61N 5/10* (2013.01); *A61N 5/1042* (2013.01); *A61B 6/508* (2013.01)
USPC .............................................. 378/4; 378/65

(58) Field of Classification Search
CPC . A61N 5/1069; A61N 5/1042; A61N 5/0306; A61N 5/1047; A61B 6/0306
USPC ........................................... 378/4, 64, 65, 62
See application file for complete search history.

(56) References Cited

U.S. PATENT DOCUMENTS

| 2,842,706 A | 7/1958 | Dobischek et al. |
| 3,617,285 A | 11/1971 | Staudenmayer |

(Continued)

FOREIGN PATENT DOCUMENTS

| CN | 2336381 Y | 9/1999 |
| CN | 2440535 | 8/2001 |

(Continued)

OTHER PUBLICATIONS

Bentley, M.D. et al., "The Use of Microcomputed Tomography to Study Microvasculature in Small Rodents", Am. J Physiol Regulatory Integrative Comp Physiol, 282, pp. R1267-R1279, 2002.

(Continued)

*Primary Examiner* — Irakli Kiknadze

(74) *Attorney, Agent, or Firm* — Jenkins, Wilson, Taylor & Hunt, P.A.

(57) ABSTRACT

The present subject matter relates to compact, non-synchrotron microbeam radiation therapy (MRT) systems and methods for cancer research and treatment based on a carbon nanotube distributed x-ray source array technology. The systems and methods can deliver microscopically discrete x-ray radiation at peak dose rate of 10 Gy per second or higher. The x-ray radiation can be provided by a spatially distributed x-ray source array. The technology can be used, for example and without limitation, for human cancer treatment, for intraoperative radiation therapy, and for pre-clinical cancer research on animal cancer models.

12 Claims, 8 Drawing Sheets

(56) References Cited

U.S. PATENT DOCUMENTS

| | | |
|---|---|---|
| 3,733,484 A | 5/1973 | Bayard |
| 3,753,020 A | 8/1973 | Zingaro |
| 3,783,288 A | 1/1974 | Barbour et al. |
| 3,921,022 A | 11/1975 | Levine |
| 3,932,756 A | 1/1976 | Cowell et al. |
| 4,012,656 A | 3/1977 | Norman et al. |
| 4,145,614 A | 3/1979 | Kowalski |
| 4,253,221 A | 3/1981 | Cochran, Jr. et al. |
| 4,289,969 A | 9/1981 | Cooperstein et al. |
| 4,382,184 A | 5/1983 | Wernikoff |
| 4,712,226 A | 12/1987 | Horbaschek |
| 4,780,612 A | 10/1988 | Klatt |
| 4,809,308 A | 2/1989 | Adams et al. |
| 4,926,452 A | 5/1990 | Baker et al. |
| 4,958,365 A | 9/1990 | Sohval et al. |
| 5,129,850 A | 7/1992 | Kane et al. |
| 5,138,237 A | 8/1992 | Kane et al. |
| 5,245,648 A | 9/1993 | Kinney et al. |
| 5,305,363 A | 4/1994 | Burke et al. |
| 5,371,778 A | 12/1994 | Yanof et al. |
| 5,377,249 A | 12/1994 | Wiesent et al. |
| 5,390,112 A | 2/1995 | Tam |
| 5,412,703 A | 5/1995 | Goodenough et al. |
| 5,424,054 A | 6/1995 | Bethune et al. |
| 5,557,105 A | 9/1996 | Honjo et al. |
| 5,578,821 A | 11/1996 | Meisberger et al. |
| 5,594,770 A | 1/1997 | Bowles et al. |
| 5,616,368 A | 4/1997 | Jin et al. |
| 5,623,180 A | 4/1997 | Jin et al. |
| 5,637,950 A | 6/1997 | Jin et al. |
| 5,648,699 A | 7/1997 | Jin et al. |
| 5,692,028 A | 11/1997 | Geus et al. |
| 5,726,524 A | 3/1998 | Debe |
| 5,754,437 A | 5/1998 | Blazo |
| 5,764,683 A | 6/1998 | Swift et al. |
| 5,773,834 A | 6/1998 | Yamamoto et al. |
| 5,773,921 A | 6/1998 | Keesmann et al. |
| 5,834,783 A | 11/1998 | Muraki et al. |
| 5,844,963 A | 12/1998 | Koller et al. |
| 5,910,974 A | 6/1999 | Kuhn et al. |
| 5,973,444 A | 10/1999 | Xu et al. |
| RE36,415 E | 11/1999 | McKenna |
| 5,976,444 A | 11/1999 | Pearson et al. |
| 6,019,656 A | 2/2000 | Park et al. |
| 6,028,911 A | 2/2000 | Kawahara |
| 6,057,637 A | 5/2000 | Zettl et al. |
| 6,087,765 A | 7/2000 | Coll et al. |
| 6,097,138 A | 8/2000 | Nakamoto |
| 6,097,788 A | 8/2000 | Berenstein et al. |
| 6,125,167 A | 9/2000 | Morgan |
| 6,178,226 B1 | 1/2001 | Hell et al. |
| 6,192,104 B1 | 2/2001 | Adams et al. |
| 6,250,984 B1 | 6/2001 | Jin et al. |
| 6,259,765 B1 | 7/2001 | Baptist |
| 6,271,923 B1 | 8/2001 | Hill |
| 6,277,318 B1 | 8/2001 | Bower et al. |
| 6,280,697 B1 | 8/2001 | Zhou et al. |
| 6,297,592 B1 | 10/2001 | Goren et al. |
| 6,333,968 B1 | 12/2001 | Whitlock et al. |
| 6,334,939 B1 | 1/2002 | Zhou et al. |
| 6,350,628 B1 | 2/2002 | Cheng et al. |
| 6,376,973 B1 | 4/2002 | Blanchet-Fincher et al. |
| 6,385,292 B1 | 5/2002 | Dunham et al. |
| 6,440,761 B1 | 8/2002 | Choi |
| 6,445,122 B1 | 9/2002 | Chuang et al. |
| 6,456,691 B2 | 9/2002 | Takahashi et al. |
| 6,459,767 B1 | 10/2002 | Boyer et al. |
| 6,470,068 B2 | 10/2002 | Cheng |
| 6,498,349 B1 | 12/2002 | Thomas et al. |
| 6,510,195 B1 | 1/2003 | Chappo et al. |
| 6,529,575 B1 | 3/2003 | Hsieh |
| 6,545,396 B1 | 4/2003 | Ohki et al. |
| 6,553,096 B1 | 4/2003 | Zhou et al. |
| 6,560,309 B1 | 5/2003 | Becker et al. |
| RE38,223 E | 8/2003 | Keesmann et al. |
| 6,621,887 B2 | 9/2003 | Albagli et al. |
| 6,630,772 B1 | 10/2003 | Bower et al. |
| 6,650,730 B2 | 11/2003 | Bogatu et al. |
| 6,672,926 B2 | 1/2004 | Liu et al. |
| 6,674,837 B1 | 1/2004 | Taskar et al. |
| 6,754,300 B2 | 6/2004 | Hsieh et al. |
| 6,760,407 B2 | 7/2004 | Price et al. |
| RE38,561 E | 8/2004 | Keesmann et al. |
| 6,787,122 B2 | 9/2004 | Zhou |
| 6,850,595 B2 | 2/2005 | Zhou et al. |
| 6,852,973 B2 | 2/2005 | Suzuki et al. |
| 6,876,724 B2 | 4/2005 | Zhou et al. |
| 6,950,493 B2 | 9/2005 | Besson |
| 6,965,199 B2 | 11/2005 | Stoner et al. |
| 6,980,627 B2 | 12/2005 | Qiu et al. |
| 7,027,558 B2 | 4/2006 | Ghelmansarai et al. |
| 7,046,757 B1 | 5/2006 | Bani-Hashemi et al. |
| 7,082,182 B2 | 7/2006 | Zhou et al. |
| 7,085,351 B2 | 8/2006 | Lu et al. |
| 7,147,894 B2 | 12/2006 | Zhou et al. |
| 7,220,971 B1 | 5/2007 | Chang et al. |
| 7,227,924 B2 | 6/2007 | Zhou et al. |
| 7,245,692 B2 | 7/2007 | Lu et al. |
| 7,359,484 B2 | 4/2008 | Qiu et al. |
| 7,420,174 B2 | 9/2008 | Kurita et al. |
| 7,486,772 B2 | 2/2009 | Lu et al. |
| 7,684,537 B2 | 3/2010 | Imai et al. |
| 7,741,624 B1 | 6/2010 | Sahadevan |
| 7,751,528 B2 | 7/2010 | Zhou et al. |
| 7,835,492 B1 | 11/2010 | Sahadevan |
| 7,902,530 B1 | 3/2011 | Sahadevan |
| 8,155,262 B2 | 4/2012 | Zhou et al. |
| 8,189,893 B2 | 5/2012 | Zhang et al. |
| 8,358,739 B2 | 1/2013 | Lu |
| 8,600,003 B2 | 12/2013 | Zhou et al. |
| 2001/0019601 A1 | 9/2001 | Tkahashi et al. |
| 2002/0085674 A1 | 7/2002 | Price et al. |
| 2002/0094064 A1 | 7/2002 | Zhou et al. |
| 2002/0110996 A1 | 8/2002 | Yaniv et al. |
| 2002/0140336 A1 | 10/2002 | Stoner et al. |
| 2002/0159565 A1 | 10/2002 | Muller et al. |
| 2002/0171357 A1 | 11/2002 | Sun et al. |
| 2002/0191751 A1 | 12/2002 | Bogatu et al. |
| 2002/0193040 A1 | 12/2002 | Zhou |
| 2003/0002627 A1 | 1/2003 | Espinosa et al. |
| 2003/0002628 A1 | 1/2003 | Wilson et al. |
| 2003/0048868 A1 | 3/2003 | Bailey et al. |
| 2003/0102222 A1 | 6/2003 | Zhou et al. |
| 2003/0103666 A1 | 6/2003 | Edic et al. |
| 2003/0142790 A1 | 7/2003 | Zhou et al. |
| 2003/0198318 A1 | 10/2003 | Price et al. |
| 2004/0017888 A1 | 1/2004 | Seppi et al. |
| 2004/0028183 A1 | 2/2004 | Lu et al. |
| 2004/0036402 A1 | 2/2004 | Keesmann et al. |
| 2004/0065465 A1 | 4/2004 | Chappo et al. |
| 2004/0108298 A1 | 6/2004 | Gao |
| 2004/0114721 A1 | 6/2004 | Qiu et al. |
| 2004/0213378 A1 | 10/2004 | Zhou et al. |
| 2004/0240616 A1 | 12/2004 | Qui et al. |
| 2004/0256975 A1 | 12/2004 | Gao et al. |
| 2005/0028554 A1 | 2/2005 | Wanner et al. |
| 2005/0084073 A1 | 4/2005 | Seppi et al. |
| 2005/0117701 A1 | 6/2005 | Nelson et al. |
| 2005/0133372 A1 | 6/2005 | Zhou et al. |
| 2005/0175151 A1 | 8/2005 | Dunham et al. |
| 2005/0226361 A1 | 10/2005 | Zhou et al. |
| 2005/0226371 A1 | 10/2005 | Kautzer et al. |
| 2005/0269559 A1 | 12/2005 | Zhou et al. |
| 2005/0281379 A1 | 12/2005 | Qiu et al. |
| 2006/0018432 A1 | 1/2006 | Zhou et al. |
| 2006/0291711 A1 | 12/2006 | Jabri et al. |
| 2007/0009081 A1 | 1/2007 | Zhou et al. |
| 2008/0031400 A1 | 2/2008 | Beaulieu et al. |
| 2008/0069420 A1 | 3/2008 | Zhang et al. |
| 2008/0144772 A1 | 6/2008 | Yi |
| 2008/0154085 A1 | 6/2008 | Jervis |
| 2008/0292052 A1* | 11/2008 | Dilmanian et al. ............ 378/65 |
| 2010/0239064 A1 | 9/2010 | Zhou et al. |
| 2010/0329413 A1 | 12/2010 | Zhou et al. |

(56) References Cited

U.S. PATENT DOCUMENTS

FOREIGN PATENT DOCUMENTS

| | | |
|---|---|---|
| CN | 1316279 | 10/2001 |
| CN | ZL200680013859.X | 1/2011 |
| CN | ZL200810215733 | 10/2011 |
| CN | ZL200680043786.9 | 3/2013 |
| DE | 197 00 992 | 7/1998 |
| DE | 101 64 315 A1 | 8/2002 |
| DE | 101 64 318 A1 | 8/2002 |
| EP | 0 268 488 | 5/1988 |
| EP | 1 050 272 A1 | 11/2000 |
| EP | 0 648 468 | 4/2005 |
| GB | 679617 | 9/1952 |
| JP | 53103392 A | 9/1978 |
| JP | A S54-027793 | 3/1979 |
| JP | 57162431 A2 | 10/1982 |
| JP | 60254615 A2 | 12/1985 |
| JP | A S61-142644 | 6/1986 |
| JP | 06163381 A2 | 6/1994 |
| JP | 09-180894 A | 7/1997 |
| JP | 11-111158 | 4/1999 |
| JP | A H11-116218 | 4/1999 |
| JP | 11-260244 | 9/1999 |
| JP | 08264139 A | 10/1999 |
| JP | 2000-208028 | 7/2000 |
| JP | 2000251826 A2 | 9/2000 |
| JP | A 2001-048509 | 2/2001 |
| JP | 2001190550 A | 7/2001 |
| JP | 2001250496 A | 9/2001 |
| JP | 2003100242 A | 4/2003 |
| TW | 00319886 | 11/1997 |
| TW | 0379354 B | 1/2000 |
| TW | 0439303 B | 6/2001 |
| TW | 0527624 B | 4/2003 |
| TW | 0529050 B | 4/2003 |
| WO | WO 98/57349 | 12/1998 |
| WO | WO 00/51936 A3 | 9/2000 |
| WO | WO 01/58525 | 8/2001 |
| WO | WO 02/03413 | 1/2002 |
| WO | WO 02/31857 | 4/2002 |
| WO | WO 03/012816 A2 | 2/2003 |
| WO | WO 2004/061477 | 7/2004 |
| WO | WO 2004/096050 | 11/2004 |
| WO | WO 2004/097889 | 11/2004 |
| WO | WO 2005/079246 | 1/2005 |

OTHER PUBLICATIONS

Bonard et al., "Field emission from single-wall carbon nanotube films", Appl. Phys. Lett., vol. 73(7), No. 7, pp. 918-920, (Aug. 17, 1998).

Bower et al., "Synthesis and structure of pristine and alkali-metal-intercalated single-walled carbon nanotubes", Appl. Phys., A 67, pp. 47-52 (1998).

Bower, C. et al., "Fabrication and Field Emission Properties of Carbon Nanotube Cathodes", Mat. Res. Soc. Symp. Proc., vol. 593, pp. 215-220, 2000.

Brock et al., "Hadamard Transform Time-of-Flight Mass Spectrometry," Analytical Chemistry, vol. 70, No. 18, Sep. 15, 1998.

Brodie et al., "Vacuum Microelectronics", Advance in Electronics and Electron Physics, edited by P.W. Hawkes, vol. 83, pp. 1-106 (1992).

Bushong, S.C., "Radiologic Science for Technologist," Physics, Biology, and Protection, 6th Edition, Mosby, Inc., 1997 (pp. 107-125).

Cassell et al., "Large Scale CVD Synthesis of Single-Walled Carbon Nanotubes", J. Phys. Chem., B 103, pp. 6484-6492 (Jul. 20, 1999).

Charbonnier et al., "Resolution of Field-Emmision X-Ray Sources," Radiology, vol. 117: pp. 165-172 (Oct. 1975).

Cheng et al., "Dynamic radiography using a carbon-nanotube-based field emmision x-ray source," Review of Scientific Instruments, vol. 75, No. 10: pp. 3264-3267 (Oct. 2004).

Cheng et al., "Electron Field Emission from Carbon Nanotubes," C.R. Physique, pp. 1021-1033 (2003).

de Heer et al., "A Carbon Nanotube Field-Emission Electron Source", Science, vol. 270, pp. 1179-1180 (Nov. 17, 1995).

Dobbins III et al., "Digital x-ray tomosynthesis: current state of the art and clinical potential," Phys. Med. Biol. 48 (2003) R65-R106.

Feldkamp L.A. et al., "Practical Cone-Beam Algorithm", J. Opt. Soc. Am., 1(a):612-619, 1984.

Gao et al., "Fabrication and Electron Field Emmision Properties of Carbon Nanotube Films by Electrophoretic Deposition," Advanced Materials, vol. 13, No. 23 (2001) pp. 1770-1773.

Geis et al., "Diamond emitters fabrication and theory", J. Vac. Sci. Technol. B, vol. 14, No. 3, pp. 2060-2067, May/Jun. 1996.

Hallenbeck, "Clinical Evaluation of the 350-kV Chest Radiography System," Radiology, vol. 117: pp. 1-4 (1974).

Hu, J. et al., "Chemistry and Physics in One Dimension: Synthesis and Properties of Nanowires and Nanotubes", Accounts of Chemical Research, vol. 32, pp. 435-445, 1999.

Jerri, "The Shannon Samplin Theorem—Its Various Extensions and Applications: A Tutorial Review," IEEE, vol. 65, No. 11, pp. 1565-1596 (1977).

Journet et al., "Large-scale production of single-walled carbon nanotubes by the electric-arc technique", Nature, vol. 388, pp. 756-760 (Aug. 21, 1997).

Kruger et al., "Tomosynthesis Applied to Digital Subtraction Angiography," Radiology, V152, pp. 805-808 (1984).

Kumar et al., "Diamond-based field emission flat panel displays", Solid State Technology, vol. 38, pp. 71-74 (May 1995).

Lalush, "Feasibility of Transmission Micro-CT with Two Fan-Beam Sources," Proceedings of 26th Annual Int'l Conf on IEEE EMBS, pp. 1283-1286, Sep. 5, 2004.

Lee et al., "Novel Micro-CT Based on a Carbon Nanotube Field Emission X-ray Source," 2003 Radiological Society of North American Meeting, Abstract Code A21-182, Nov. 30, 2003.

Lee et al., "Pulsed X-Ray Imaging of Small Animals Using a Carbon Nanotube Based X-Ray Source" presented at the Academy of Molecular Imaging Annual Meeting, Orlando, FL, Mar. 2004, Molecular Imaging and Biology, vol. 6, No. 2, Abstract No. 41, p. 80.

Moore et al., "Three-Dimensional X-Ray Laminography as a Tool for Detection and Characterization of BGA Package Defects", IEEE Transactions on Components and Packaging Technologies. vol. 25, No. 2, Jun. 2002.

Nyquist, "Certain Topics in Telegraphic Transmission Theory," IEEE, vol. 2, No. 2, pp. 208-305 (2002).

Okano et al., "Electron emission from nitrogen-doped pyramidal-shape diamond and its battery operation", Appl. Phys. Lett., vol. 70, No. 16, pp. 2201-2203 (Apr. 21, 1997).

Okano et al., "Fabrication of a diamond field emitter array", Appl. Phys. Lett., vol. 64, No. 20, pp. 2742-2744 (May 16, 1994).

Okazaki et al., "A New Emission Spectrum of Au2 in the Gas Evaporation Technique: 761-809 nm", Jpn. J. Appl. Phys., vol. 37, Pt. 1, No. 1, pp. 349-350 (Jan. 1998).

Resat et al., "Microbeam developments and applications: A low linear energy transfer perspective," Cancer and Metastasis Reviews 23: p. 323-331 (2004).

Ribbing et al., "Diamond membrane based sructures for miniature X-ray sources," Diamond and Related Materials, vol. 11: pp. 1-7 (2002).

Rinzler et al., "Unraveling Nanotubes: Field Emission from an Atomic Wire", Science, vol. 269, pp. 1550-1553 (Sep. 15, 1995).

Saito, Y. et al., "Field Emission Patterns from Single-Walled Carbon Nanotubes", Jpn. J. Appl. Phys., vol. 36, pp. L1340-L1342, Part 2, No. 10A, Oct. 1, 1997.

Saito, Y. et al., "Cathode Ray Tube Lighting Elements with Carbon Nanotube Field Emitters", Jpn. J. Appl. Phys., vol. 37, pp. L346-L348, Part 2, No. 3B, Mar. 15, 1998.

Shannon, "Communication in the Presence of Noise," IEEE, vol. 86, No. 2, pp. 447-108 (1998).

Slatkin, D et al., Proc. Natl. Acac. Sci. USA, vol. 92, pp. 8783-8787, 1995.

Sloane, "Multiplexing Methods in Spectroscopy," Mathematics Magazine, vol. 52, No. 2 (Mar. 1979), 71-80.

(56) References Cited

OTHER PUBLICATIONS

Sugie et al., "Carbon nanotubes as electron source in an x-ray tube," Applied Physics Letters, vol. 78, No. 17: pp. 2578-2580 (2001).
Tang, X. P. et al., "Electronic Structures of Single-Walled Carbon Nanotubes Determined by NMR", Science, vol. 288, pp. 492-494 (Apr. 21, 2000).
Thess, A. et al., "Crystalline Ropes of Metallic Carbon Nanotubes", Science, vol. 273, pp. 483-487 (Jul. 26, 1996).
Traedo, "A Thousand Points of Light: The Hadamard Transform in Chemical Analysis and Instrumentation," Analytical Chemistry. vol. 61, No. 11, Jun. 1, 1989.
Vogel et al., "A New Method of Multiplanar Emission Tomography Using a Seven Pinhole Collimator and an Anger Scintillation Camera," Jour. Nuclear Medicine, vol. 19, No. 6, pp. 648-654, 1978.
Wang et al., "Field Emission From Nanotube Bundle Emitters at Low Fields", App. Phys. Lett., 70(24), pp. 3308-3310, Jun. 16, 1997.
Wang et al., "A nanotube-based field-emission flat panel display", Appl. Phys. Lett., vol. 72, No. 2, pp. 2912-2913 (Jun. 1, 1998).
Weinstein et al., "Data Transmission by Frequency-Division Multiplexing Using the Discrete Fourier Transform," IEEE Trans. on Commun. Tech., vol. Com-19, No. 5, pp. 628-634, Oct. 1971.
Weisstein, "CRC Concise Encyclopedia of Mathematics," Second Ed., pp. 1, 54, 1092-1097, 1936, 2046 and 2615 (2003).
Yagishita et al., "Effects of Cleavage on Local Cross-Sectional Stress Distribution in Trench Isolation Structure", Jpn. J. Appl. Phys., vol. 36, pp. 1335-1340 (Mar. 1997).
Yue et al., "Generation of continuous and pulsed diagnostic imaging x-ray radiation using a carbon nontube based field emission cathode," Applied Physics Letters, vol. 81, No. 2: pp. 355-357 (F) Jul. 8, 2002.
Zhang et al., "Multiplexing radiography using a carbon nanotube based x-ray source," Applied Physics Letters, vol. 89, Aug. 2006.
Zhang et al., "Stationary scanning x-ray source based on carbon nanotube field emitters," Applied Physics Letters, vol. 86, 2005.
Zhou et al., "Materials Science of Carbon Nanotubes: Fabrication, Integration, and Properties of Macroscopic Structures of Carbon Nanotubes", Acc. Chem. Res., vol. 35, pp. 1045-1053, 2002.
Zhu et al., "Low-Field Electron Emission from Updoped Nanostructured Diamond", Science, vol. 282, 1471-1473 (Nov. 20, 1998).
Zhu, W. et al., "Large Current Density from Carbon Nanotube Filed Emitters", Appl. Phys. Lett., American Institute of Physics, vol. 75, No. 6, Aug. 9, 1999, pp. 873-875.
Non-final Office Action for U.S. Appl. No. 09/679,303 dated Jan. 16, 2002.
Final Office Action for U.S. Appl. No. 09/679,303 dated May 6, 2002.
Non-final Office Action for U.S. Appl. No. 09/679,303 dated Aug. 20, 2002.
Notice of Allowance for U.S. Appl. No. 09/679,303 dated Nov. 1, 2002.
Office Communication for U.S. Appl. No. 09/679,303 dated Feb. 6, 2003.
International Search Report for Application No. PCT/US03/00537 dated Apr. 10, 2003.
Non-final Office Action for U.S. Appl. No. 10/309,126 dated May 22, 2003.
Non-final Office Action for U.S. Appl. No. 10/051,183 dated Sep. 10, 2003.
Non-final Office Action for U.S. Appl. No. 10/309,126 dated Nov. 5, 2003.
Non-final Office Action for U.S. Appl. No. 10/309,126 dated Apr. 20, 2004.
Non-final Office Action for U.S. Appl. No. 10/051,183 dated Apr. 21, 2004.
Notice of Allowance for U.S. Appl. No. 10/309,126 dated Aug. 26, 2004.
Notice of Allowance for U.S. Appl. No. 10/051,183 dated Aug. 31, 2004.
Corrected Notice of Allowance for U.S. Appl. No. 10/309,126 dated Sep. 14, 2004.
Non-final Office Action for U.S. Appl. No. 10/358,160 dated Sep. 21, 2004.
Office Communication for U.S. Appl. No. 10/051,183 dated Jan. 14, 2005.
International Search Report and Written Opinion for PCT/US04/12660 dated Apr. 7, 2005.
Non-final Office Action U.S. Appl. No. 10/358,160 dated Jun. 7, 2005.
Office Action—Restriction requirement U.S. Appl. No. 10/358,160 dated Oct. 26, 2005.
Notice of Allowance U.S. Appl. No. 10/358,160 dated Feb. 8, 2006.
International Search Report and Written Opinion for Application No. PCT/US05/03991 dated Jun. 22, 2006 / Aug. 14, 2006.
Non-Final Office Action for U.S. Appl. No. 11/320,515 dated Aug. 17, 2006.
Office Action—Restriction requirement for U.S. Appl. No. 11/051,332 dated Sep. 7, 2006.
International Search Report for corresponding International Application No. PCT/US05/47066 dated Oct. 6, 2006.
Notice of Allowance dated for U.S. Appl. No. 11/051,332 dated Dec. 28, 2006.
International Preliminary Report on Patentability for PCT/US04/12660 dated May 9, 2007.
International Search Report for PCT/US06/37046 dated May 21, 2007.
Korean Intellectual Property Office (KIPO) Office Action for Korean Patent Application No. 10-2004-7011373 dated Jun. 11, 2007.
European Patent Office Examination Report dated Jun. 28, 2007 for European Patent Application No. 03702044.3.
Korean Intellectual Property Office (KIPO) Office Action for Korean Patent Application No. 10-2003-700004987 dated Jul. 19, 2007.
Second Chinese Office Action for Patent Application No. 03806739.0 dated Oct. 19, 2007.
Non-final Office Action for U.S. Appl. No. 11/415,953 dated Dec. 11, 2007.
Korean Office Action for Korean Patent Application No. 10-2004-7011373 dated Dec. 18, 2007.
Taiwanese Office Action for Taiwan Patent No. 093102622 dated Dec. 21, 2007.
Examination Report from European Patent Office dated Mar. 3, 2008 for European Patent Application No. 03702044.3.
Third Chinese Office Action dated Mar. 14, 2008 for Chinese Patent Application No. 01820211.X.
Non-final Office Action for U.S. Appl. No. 10/970,384 dated Apr. 8, 2008.
Office Action—Restriction requirement for U.S. Appl. No. 11/415,953 dated May 22, 2008.
Office Action from Canadian Patent Office dated May 27, 2008 for Canadian Application No. 2,424,826.
Japanese Patent Office Action for JP No. 2003-562962 for corresponding PCT No. US03/00537 dated Jun. 20, 2008.
Office Action from Japanese Patent Office for Japanese Patent Application No. 2003-580561 for corresponding PCT No. US03/06345 dated Sep. 3, 2008.
Decision on Granting of Patent Right has been issued from the Chinese Patent Office for Chinese Patent Application No. 01820211.X (PCT/US01/30027 dated Sep. 26, 2008.
International Search Report and Written Opinion for PCT Application No. PCT/US08/70477 dated Oct. 1, 2008.
First Office Action from Japanese Patent Office dated Oct. 17, 2008 for Japanese Patent Application No. 2002-535152, based on PCT/US01/30027.
First Office Action from Japanese Patent Office dated Jan. 6, 2009 for JP Application No. 2006-513282.
Notice of Publication for Chinese Patent Application No. 200810215733.1 (Publication No. 101352353) dated Jan. 28, 2009.
Confirmation of issuance of Chinese Patent No. ZL01820211.X corresponding to PCT/US01/30027 dated Feb. 4, 2009.
Confirmation that Chinese Application 093102622 issued on Mar. 1, 2009 as Patent No. TW I307110.
First Office Action from Chinese Patent Office dated Mar. 6, 2009 for Chinese Patent Application No. 200480017120.7.

(56) References Cited

OTHER PUBLICATIONS

Japanese Final Office Action for Japanese Patent Application No. 2003-562962 based on PCT/US03/00537 dated Mar. 30, 2009.
First Office Action from Chinese Patent Office dated Apr. 24, 2009 for Chinese Patent Application No. 200710003710.X.
Office Action—Final for U.S. Appl. No. 11/441,281 dated Jun. 4, 2009.
Supplementary European Search Report for European Patent Application No. 01981327.8 dated Jun. 22, 2009.
Non-Final Office Action for U.S. Appl. No. 12/176,056 dated Sep. 2, 2009.
First Office Action from Chinese Patent Office for Chinese Patent Application Serial No. 200680013859.X dated Sep. 25, 2009.
Supplementary European Search report dated Oct. 7, 2009 for EPO Application No. 04 77 5902 (PCT/US2004012660).
Second Office Action from Japanese Patent Office dated Dec. 7, 2009 for Japanese Patent Application No. 2002-535152.
Decision on Rejection issued from the Chinese Patent Office dated Dec. 11, 2009 for Chinese Application No. 200710003710.X.
U.S. Appl. No. 12/655,825, filed Jan. 7, 2010 entitled "System and Method for All Field Simultaneous Radiation Therapy and Concealed Object Screening . . . "
Non-final Office Action for U.S. Appl. No. 11/441,281 dated Jan. 11, 2010.
Second Office Action corresponding to Chinese Patent Application No. 200680013859 dated Apr. 30, 2010.
First Office Action corresponding to Chinese Patent Application No. 200680043786.9 dated Jul. 6, 2010.
Final Office Action for U.S. Appl. No. 11/441,281 dated Sep. 30, 2010.
Non-Final Office Action for U.S. Appl. No. 11/526,217 dated Oct. 13, 2010.
Non-Final Office Action for U.S. Appl. No. 11/804,897 dated Nov. 8, 2010.
Second Office Action for CN Appl. No. 2004-80017120.7 dated Nov. 17, 2010.
Third Office Action for CN Appl. No. 2008-10215733.1 dated Dec. 14, 2010.
Third-Party Submission against U.S. Appl. No. 12/688,425 dated Feb. 28, 2011.
Second Office Action for CN Appl. No. 2006-80043786.9 dated Mar. 2, 2011.
Non-Final Office Action for U.S. Appl. No. 11/441,281 dated Mar. 15, 2011.
First Office Action for CN Appl. No. 200880107680.X dated Apr. 7, 2011.
Final Office Action for U.S. Appl. No. 11/526,217 dated May 6, 2011.
Notification to Grant for Chinese Patent Application No. 200810215733.1 dated Jun. 2, 2011.
Notification to Grant for Chinese Patent Application No. 200480017120.7 dated Jul. 12, 2011.
Final Office Action for U.S. Appl. No. 11/804,897 dated Jul. 14, 2011.
Final Office Action for U.S. Appl. No. 11/526,217 dated Aug. 19, 2011.
Japanese Office Action for JP Appl. No. 2008-532428 dated Sep. 20, 2011.
Reexamination Notice for CN Appl No. 200710003710.X dated Sep. 21, 2011.
Non-Final Office Action for U.S. Appl. No. 11/441,281 dated Oct. 19, 2011.
European Search Report for EP 06815214 dated Oct. 25, 2011.
Notice of Allowance for U.S. Appl. No. 11/526,217 dated Dec. 14, 2011.
Notice of Allowance for U.S. Appl. No. 11/804,897 dated Jan. 6, 2012.
Third Office Action for CN Appl. No. 2006-80043786.9 dated Feb. 2, 2012.
Second Reexamination Notice for CN Appl No. 200710003710.X dated Mar. 2012.
Chinese Notice of Grant for Application No. 200680043786.9 dated Nov. 5, 2012.
Notice of Allowance for U.S. Appl. No. 12/875,260 dated Dec. 21, 2012.
Chinese Office Action for Application No. 200880107680.X dated Jan. 14, 2013.
Chinese Office Action for Application No. 200710003710.X dated Feb. 5, 2013.
Chinese Notice of Grant for Application No. 200880107680.X dated Aug. 6, 2013.
Notice of Allowance for U.S. Appl. No. 12/688,425 dated Jul. 31, 2013.
Chinese Office Action for Application No. 201010142047.3 dated Aug. 21, 2013.
Chinese Office Action for Application No. 201010142047.3 dated Mar. 5, 2014.
Chinese Decision to Grant for Application No. 201010142047.3 dated Sep. 9, 2014.

* cited by examiner

COMPACT MICROBEAM RADIATION THERAPY SYSTEMS AND METHODS FOR CANCER TREATMENT AND RESEARCH

CROSS-REFERENCE TO RELATED APPLICATIONS

This application is a continuation of and claims priority to U.S. patent application Ser. No. 12/688,425 filed Jan. 15, 2010, which claims the benefit of and priority to U.S. Provisional Application No. 61/205,240, filed Jan. 16, 2009, the entire disclosures of which are herein incorporated by reference.

GOVERNMENT INTEREST

This invention was made with government support under Grant Nos. U54 CA 119343 and 1R21 CA 118351-01 awarded by the National Cancer Institute. The government has certain rights in the invention.

TECHNICAL FIELD

The subject matter disclosed herein relates generally to radiotherapy systems and methods. More particularly, the subject matter disclosed herein relates to microbeam radiotherapy systems and methods for cancer treatment and research. Microbeam Radiotherapy (MRT) radiation can be characterized by its microscopically discrete spatial radiation distribution (beam width is less than 1 millimeter and beam separation is several millimeters) and ultra-high dose rate (10 Gy/s or higher).

BACKGROUND

The fundamental challenge of radiotherapy is to treat cancer patients effectively and safely. Current radiotherapy systems and methods provide excellent benefits for patients with early stage and radiosensitive cancers, but these benefits diminish for patients with radioresistant tumors (e.g., brain or pancreas cancers) and patients with late stage tumors. For these patients, the radiation needed to eradicate the tumor can cause intolerable or fatal radiation damage. This is especially the case for pediatric patients, whose rapidly developing normal tissues are often more radiosensitive than their tumors, and who therefore cannot tolerate radiotherapy that would be curative for adults with the same disease. As a result, normal tissue collateral damage is a major limitation in current radiotherapy, preventing effective radiotherapy treatments for cancer patients of a young age, patients with central nerve system cancers, radioresistant cancers, and late stage cancer with large tumors. These cancer patients currently have a poor prognosis.

Microbeam Radiotherapy (MRT) is a unique form of radiation that has shown an extraordinary ability to eradicate tumors while sparing normal tissue in numerous animal studies. MRT utilizes multiple narrow but well separated x-ray planar beams (i.e., "microbeams") and delivers radiation at extremely high dose rate. MRT radiation differs from conventional radiotherapy radiations in two aspects: dose spatial discreteness and dose temporal rate. In conventional therapy, the dose rate is about 100 times lower and the dose distribution is microscopically continuous in space. The current solution, which is not always effective, is to use multiple treatments at 2 Gy per treatment. In contrast, animal studies have shown that single treatments at a dose level of several hundred Gy (e.g., about $10^2$ Gy or greater) can eradicate a tumor while sparing normal tissue, including developing tissue in the central nervous system.

There are currently two hypotheses for the mechanism by which MRT can provide tumor eradication while sparing normal tissue. First, it is believed that tumor microvasculature does not repair itself well while normal tissue does. Second, there appears to be a bystander effect wherein unirradiated tumor cells die with irradiated tumor cells through cell-cell signaling (See, e.g., D. Slatkin et al., *Proc. Natl. Acac. Sci. USA, Vol 92*, pp 8783-8787, 1995). However, the underlying mechanism of MRT is still poorly understood. Nonetheless, MRT is extremely attractive for human application as the key challenge of radiotherapy has been how to eradicate tumors with minimal collateral damage to the host normal tissue.

Unfortunately, however, MRT requires that x-rays with an extremely high dose rate (e.g., on the order of 100 Gy/s or higher) are needed to irradiate tissues in a fraction of a second to assure minimal broadening of the micro slices due to movement of the target. This dose rate is several orders of magnitude higher than what is typically used for conventional radiation therapy.

Existing x-ray tube technologies today cannot provide a MRT dose distribution and dose rate as the MRT dose rate can be thousands of times that of state-of-art radiotherapy machines (~5 Gy/min). The high dose rate is thought to be important for minimizing the broadening (due to the object motion) of the tens of micron wide microbeam required during irradiation of live objects. A conventional x-ray tube comprises a metal filament (cathode) which emits electrons when it is resistively heated to over 1000° C. and a metal target (anode) that emits x-ray when bombarded by the accelerated electrons. The spatial resolution of an x-ray source is determined by the size of the focal spot which is the area on the x-ray anode that receives the electron beam. Because of the high operating temperature and power consumption, essentially all current commercial x-ray tubes are single-pixel devices where x-ray radiations are emitted from single focal spots on the anodes. The heat load of the anode limits the maximum x-ray flux of an x-ray tube. To generate the small MRT beam size at the ultrahigh dose rate using the current x-ray technology would require an ultrahigh electron beam density and heat load that are beyond physical possibility. For instance, the state-of-art high-power x-ray tube operating at ~100 kW delivers only about 1-10 cGy/s at patient with ~0.6 m source-object distance As a result, due to this high required dose rate, MRT has thus far been studied exclusively using synchrotron radiation, for instance at the National Synchrotron Light Source (NSLS) in the United States and at the European Synchrotron Radiation Facility (ESRF) in Grenoble, France. Therefore, in order to speed up the research that may advance the promising cancer treatment for potential human application, there is a need for compact, non-synchrotron source MRT systems and associated methods that can be widely available for cancer centers for preclinical research and clinical application.

SUMMARY

In accordance with this disclosure, compact, non-synchrotron source MRT systems and methods for microbeam radiotherapy are provided. In one aspect, a method for microbeam radiation therapy is provided. The method can comprise positioning a distributed x-ray source array about a target to be irradiated, the x-ray source array comprising a plurality of carbon-nanotube field emission x-ray sources, and simultaneously generating a plurality of x-ray microbeams from the plurality of carbon-nanotube field emission x-ray sources.

In another aspect, a microbeam radiotherapy system is provided. The system can comprise a distributed x-ray source array comprising a plurality of carbon-nanotube field emission x-ray sources, each of the x-ray sources being positioned to direct x-rays towards a common focus, a microbeam array collimation, a positioning device for aligning a target with the plurality of x-ray microbeams, and a control system in communication with each of the plurality of x-ray sources in the distributed x-ray source array for simultaneous generation of a plurality of x-ray microbeams from the plurality of x-ray sources.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which.

DETAILED DESCRIPTION

A traditional x-ray source generates x-ray radiation from a small area on the x-ray anode ("focal spot") that receives electrons. The local temperature on the anode can reach over 1500° C. when it is bombarded by the high energy electrons. The maximum x-ray dose can be limited by the heat load that can be tolerated by the anode, which is also related to the size of the focal spot. For instance, a clinical linear accelerator (LINAC) can deliver a dose of only about 5 Gy/min. In contrast, the present subject matter provides compact, non-synchrotron source MRT devices, systems, and methods that can utilize multiple separated, narrow x-ray planar or line beams to deliver radiation at a comparatively higher dose rate. The MRT devices, systems, and methods can be used, for example, for cancer treatment for humans including brain tumors and for intra-operative radiation therapy. It is also envisioned that MRT devices, systems, and methods as disclosed herein can be used for cancer research in animal models.

Figure 1A:
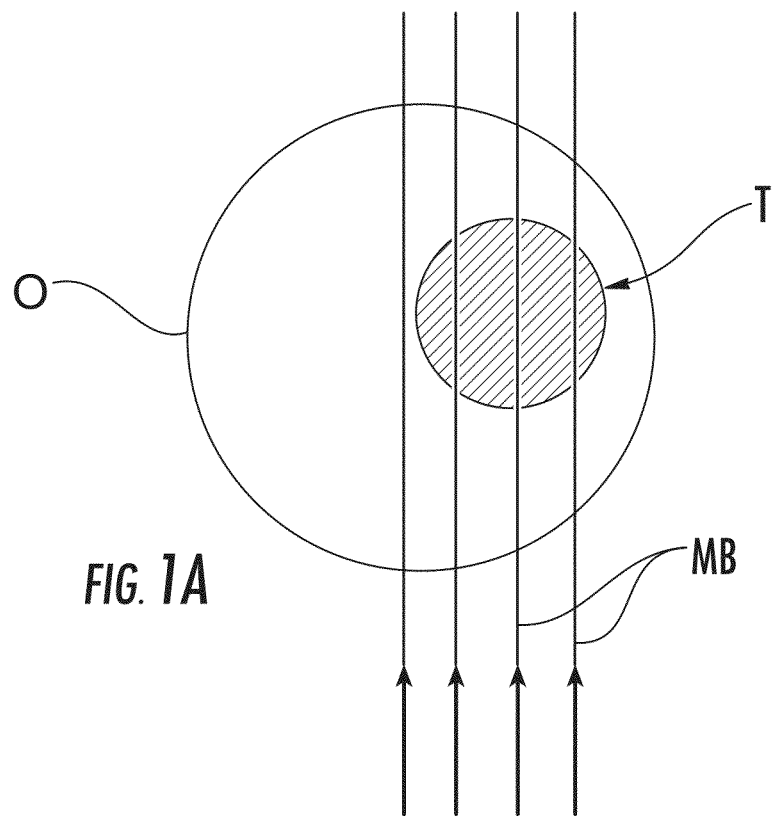
FIG. 1A is a side view of microbeam radiotherapy of a target within an object.
Figure 1B:
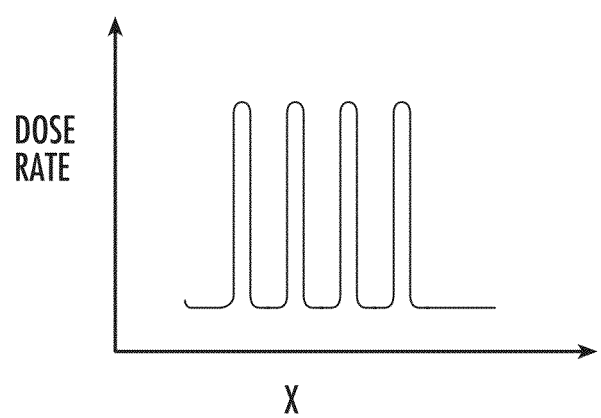
FIG. 1B is a graphical representation of the dose rate distribution across the x-ray microbeam of FIG. 1A.
Figure 2:
FIG. 2 is an image of a horizontal histological section of the hindbrain of a rat irradiated using a method for microbeam radiotherapy.

As discussed above, MRT differs from conventional radiotherapy techniques in both dose spatial discreteness and dose temporal rate. Specifically, referring to FIGS. 1A and 1B, rather than a single, broad beam that provides a substantially continuous dose distribution across the beam width, devices, systems, and methods for MRT produce a plurality of x-ray microbeams MB each having a beam width on the order of about 1 mm or smaller. As can be seen in FIG. 2, a sample irradiated using an MRT method can be identified by a plurality of distinct x-ray beam paths. The plurality of microbeams MB can be directed toward a target T (e.g., a tumor), which can be contained within an object O.

A second feature that differentiates MRT from conventional radiotherapy is the comparatively high temporal dose rate. Previously disclosed systems and methods for MRT produce x-ray using a high energy synchrotron or a conventional X-ray tube source, but each of these options has significant drawbacks as discussed above. In contrast, the presently-disclosed subject matter provides that comparatively high temporal dose rates sufficient for MRT can be achieved using a spatially distributed x-ray source array composed of a plurality of individual x-ray sources that can be positioned about object O.

In one aspect of the presently disclosed subject matter, the spatially distributed x-ray source array can be based on a carbon nanotube (CNT) distributed x-ray source array technology. For example, CNT field emitters are disclosed in U.S. Pat. No. 6,876,724, titled "Large-Area Individually Addressable Multi-Beam X-Ray System and Method of Forming Same"; U.S. Pat. No. 6,850,595, titled "X-Ray Generating Mechanism Using Electron Field Emission Cathode"; and U.S. Pat. No. 6,553,096, titled "X-Ray Generating Mechanism Using Electron Field Emission Cathode", the disclosures of which are incorporated by reference herein in their entireties.

Figure 3:
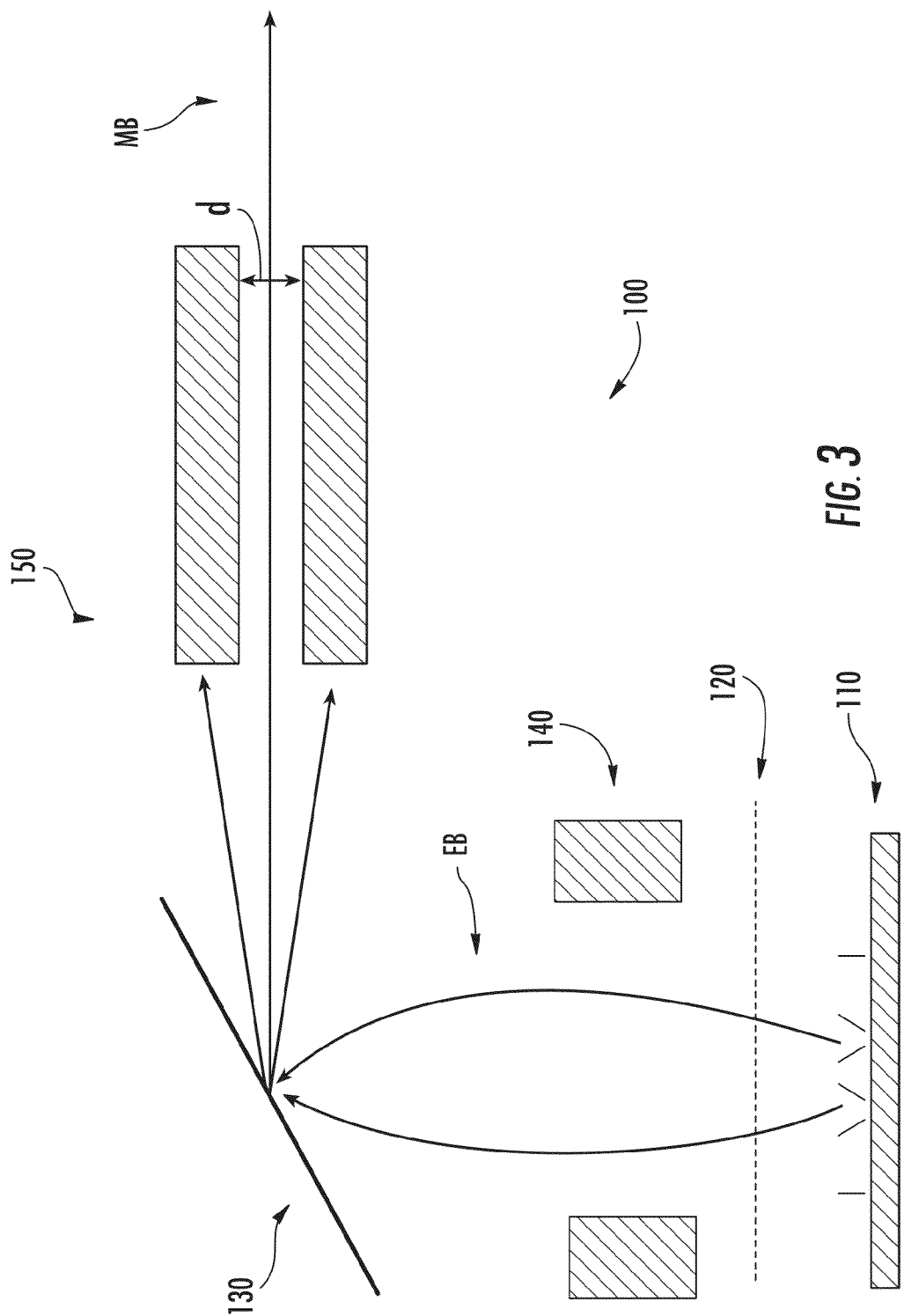
FIG. 3 is a schematic diagram of a field emission x-ray source for use with a microbeam radiotherapy system according to an embodiment of the presently disclosed subject matter.
Figure 4:
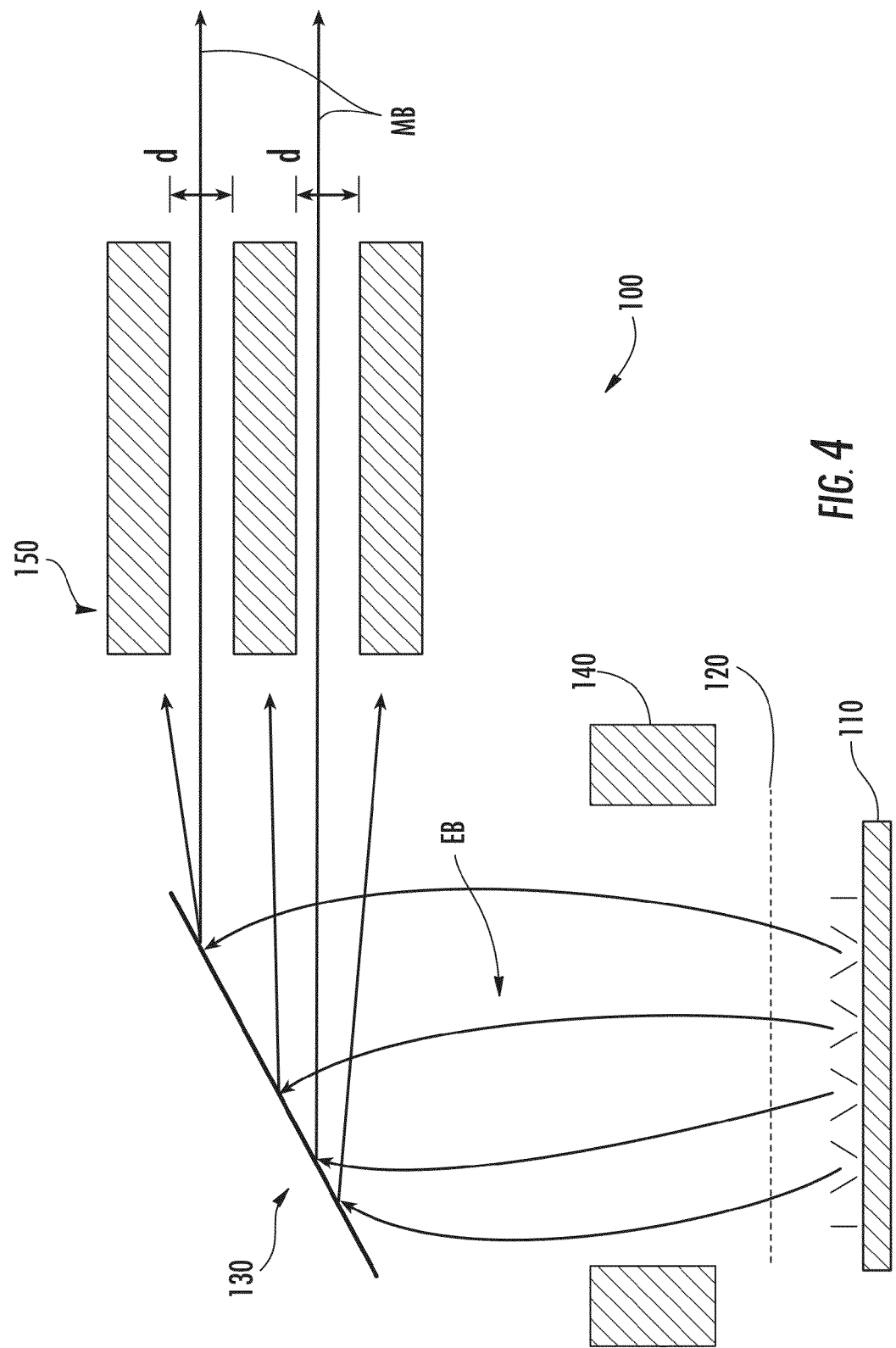
FIG. 4 is a schematic diagram of a field emission x-ray source for use with a microbeam radiotherapy system according to another embodiment of the presently disclosed subject matter.

Exemplary configurations for a field emission x-ray source are illustrated in FIGS. 3 and 4. In the exemplary configurations shown, a field emission x-ray source 100 can comprise a field emission cathode structure 110, such as, for example, a nanostructure or carbon nanotube film on a conducting substrate. A gate electrode 120 (e.g., a high melting temperature metal grid) can be positioned above cathode 110 such that applying a voltage between cathode 110 and gate electrode 120 can cause electrons to be field emitted from cathode 110, for example as an electron beam EB, and directed towards an anode 130 for generation of an x-ray beam. X-ray source 100 can further comprise a focusing electrode 140 for focusing electron beam EB before it reaches anode 130, thereby reducing the size of the focal spot on anode 130.

The system can further comprise a microbeam collimator 150, shown in FIG. 3, which can be positioned in the path of the emitted x-ray beam to allow only selected x-ray microbeams MB having a defined beam thickness d to be transmitted, thereby defining the irradiation area. In one embodiment shown in FIG. 5, for example, collimator 150 can produce fan-beam x-ray radiation with a narrow beam width (e.g., having a beam width of between about 0.01 mm and 1 mm). As a result, a thin-slice of target T can be irradiated by x-ray microbeams MB. To minimize the damage to the normal tissues, the fan-beam angle θ (i.e., the spread of the fan-beam) can also be collimated such that the x-ray radiation covers primarily the region occupied by target T. In addition, the system can also comprise a radiochromic film (e.g., Gafchromic XR-QA) positioned between each x-ray source 100 and target T. In this configuration, x-ray microbeam MB can be generated with significantly higher dose rate than what is used in clinical treatment. In another arrangement, the system can comprise a multi-slit microbeam collimator or a plurality of collimators 150, shown in FIG. 4, which can likewise be positioned in the path of the emitted x-ray beam. This arrangement can create a plurality of non-overlapping (e.g., parallel) x-ray microbeams MB emitted from each of x-ray sources 100.

Figure 5:
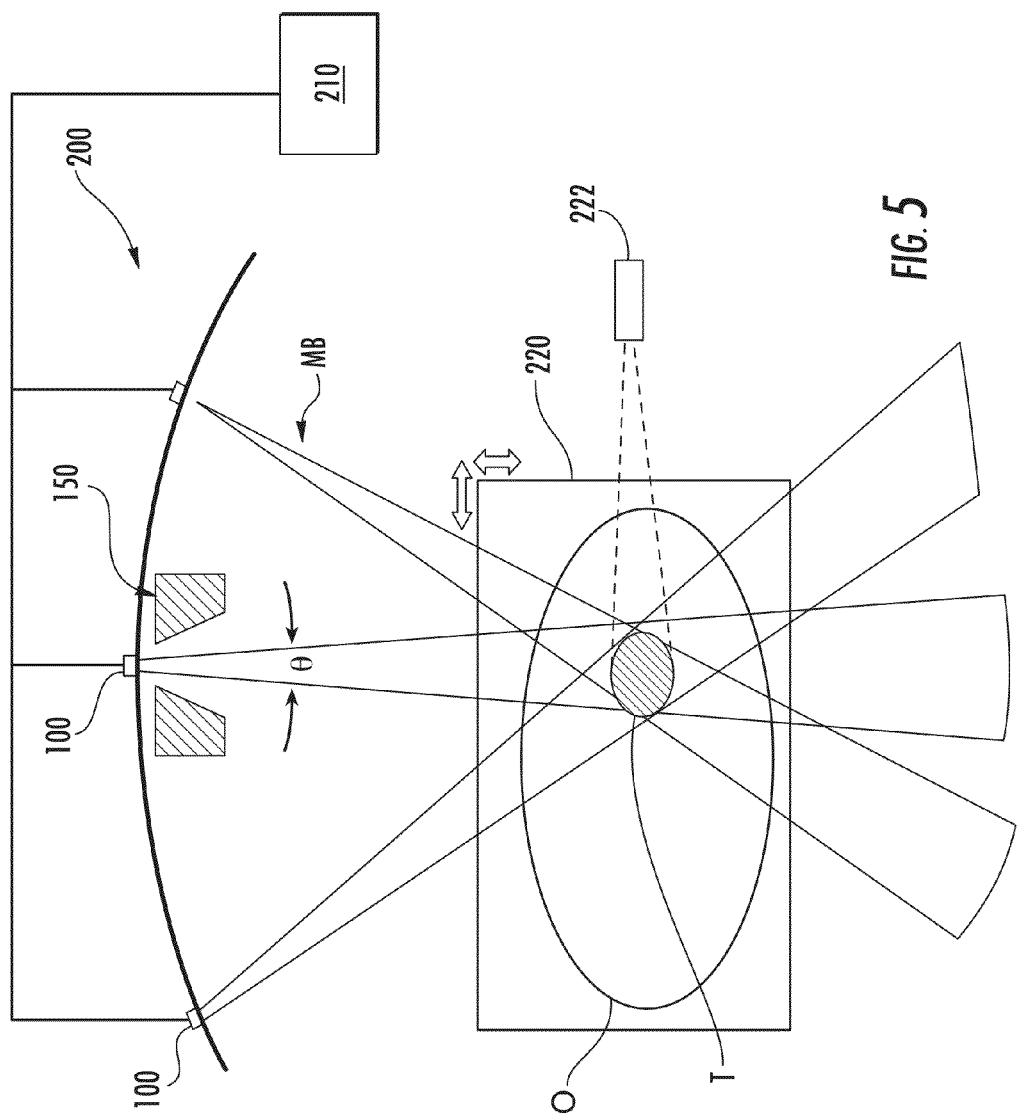
FIG. 5 is a top plan view of a microbeam radiotherapy system according to an embodiment of the presently disclosed subject matter.

To achieve the high dose rate required by MRT, a plurality of x-ray sources 100 can be assembled in a distributed x-ray source array 200 as shown in FIG. 5. Each x-ray source 100 can be a distinct element, with an independent cathode 110 and anode 130, which can be operated independently or in combination with other of the plurality of x-ray sources 100. Alternatively, x-ray source array 200 can comprise an anode ring and an opposing cathode ring inside a vacuum container. In this alternative configuration, cathode ring and anode ring can be operated collectively to produce x-ray radiation from the anode ring and irradiate target T within object O.

Figure 8:
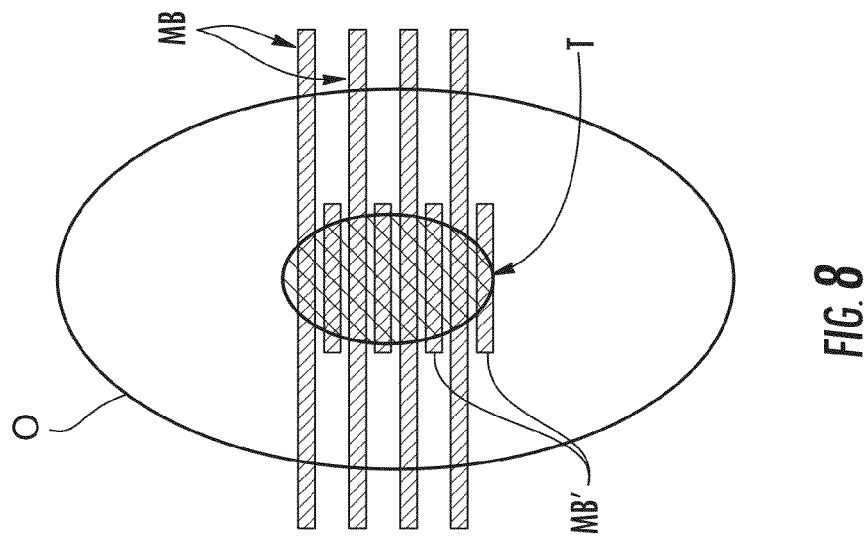
FIG. 8 is a side view of microbeam radiotherapy of a target within an object according to an embodiment of the presently disclosed subject matter.

In either arrangement, x-ray source array 200 functions as a distributed x-ray source. Instead of using one parallel x-ray beam delivering the radiation from one direction or two orthogonal beam arrays (i.e., as done in the experiments performed at the synchrotron sources), x-ray source array 200 surrounds target T to be irradiated. In this way, x-ray radiation can be delivered from multiple directions to a common focus to increase the amount of radiation received at target T without increasing the amount of radiation received at any intervening portion of object O outside of target T. In addition, each of the plurality of x-ray sources 100 can be arranged such that x-ray microbeams MB from one of x-ray sources 100 irradiate a first portion of target T, x-ray microbeams MB from a second of x-ray sources 100 irradiate a second portion of target T different from the first portion, and so on. For instance, referring to FIG. 8, a first set of x-ray microbeams MB can irradiate target T along a plurality of parallel radiation planes while a separate set of x-ray microbeams, designated MB' in FIG. 8, can irradiate target T along radiation planes that are interleaved with the radiation planes of the first set of x-ray microbeams MB. In this way, the x-ray radiation at target T has a substantially continuous dose distribution even though each individual x-ray microbeam MB does not.

As a result, by distributing the x-ray power over a large area surrounding target T, x-ray source array 200 can generate micro-planar x-ray beams with dose rates at target T that are sufficient for MRT. For example, x-ray source array 200 can generate dose rates on the order of about 0.1 to 100 Gy/sec, or it can generate much higher dose rates on the order of 500 Gy/sec. Meanwhile, portions of object O outside of target T only receive x-ray radiation from a single x-ray microbeam MB (or group of microbeams) rather than the combined radiation at the common focus, and thus the dose rate for these intervening portions can be much lower.

Figure 6:
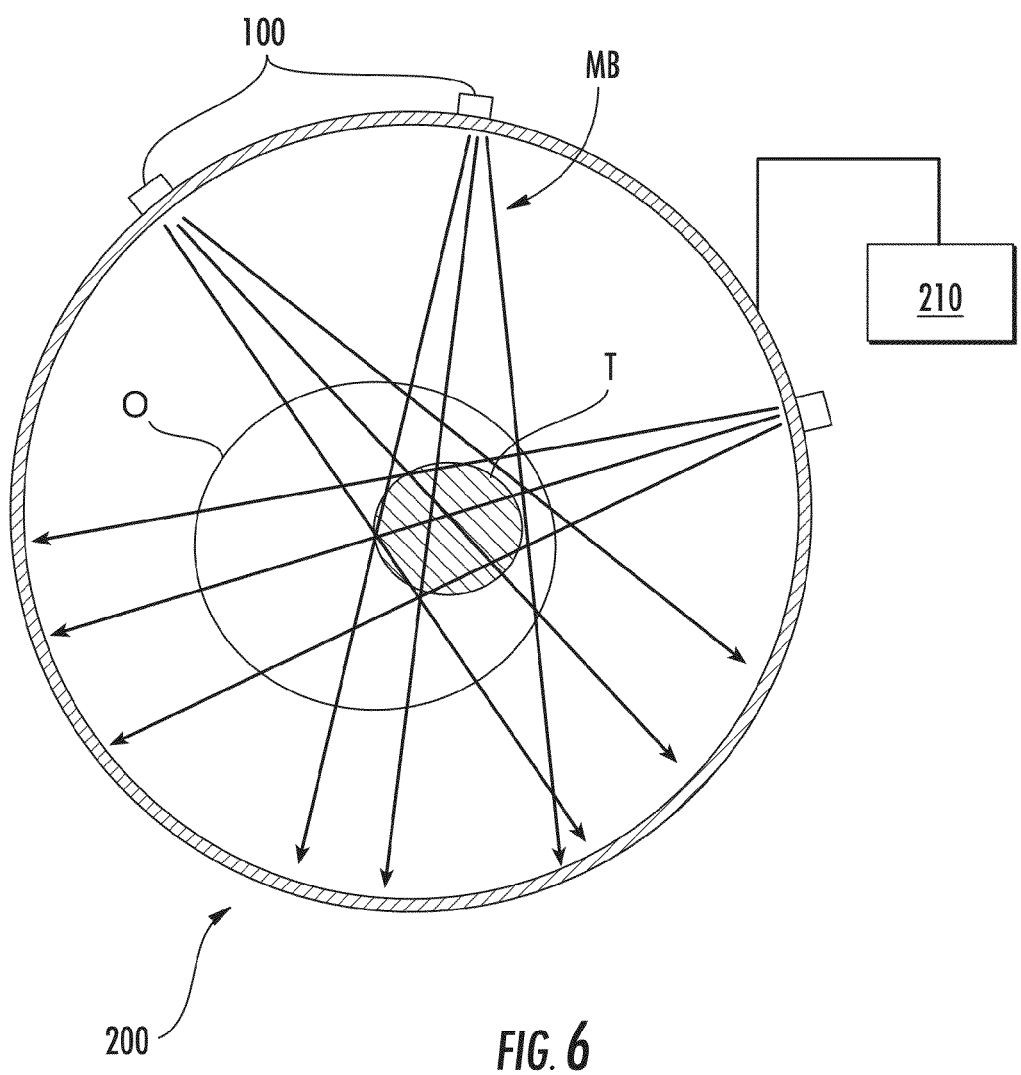
FIG. 6 is a top plan view of a microbeam radiotherapy system arranged in a ring-shaped array according to an embodiment of the presently disclosed subject matter.
Figure 7:
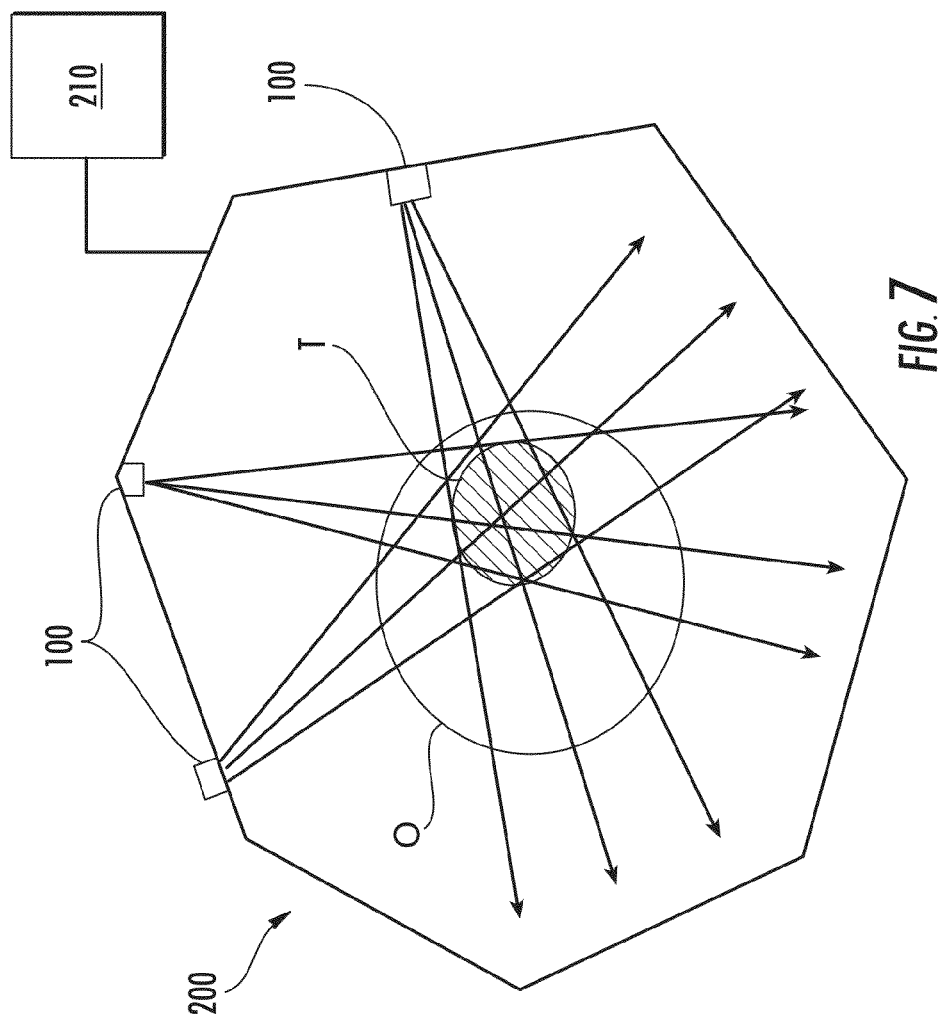
FIG. 7 is a top plan view of a microbeam radiotherapy system arranged in a polygonal array according to an embodiment of the presently disclosed subject matter.

X-ray source array 200 can be configured to be in any of a variety of geometries, such as a ring, an arc, a polygon, or a linear array. For instance, in one configuration shown in FIG. 6, x-ray source array 200 can have a ring-shaped structure. Object O can be positioned inside the ring structure, with target T at a focus of the plurality of x-ray sources 100, and a plurality of x-ray microbeams can thereby be emitted from multiple locations along a circumference of the ring towards target T. In another configuration shown in FIG. 7, x-ray source array 200 can have a polygonal structure with multiple segments, each segment essentially operating as a linear x-ray source array. Although the ring-shaped array and polygonal array configurations shown in the figures only have x-ray sources 100 on a portion of x-ray source array 200, it should be understood by those having skill in the art that x-ray sources 100 can be positioned about the entirety of x-ray source array 200 to more fully distribute the emitted x-ray microbeams MB about target T.

Compared to conventional x-ray tubes that typically generate x-rays from a small area on the x-ray anode, therefore, x-ray source array 200 distributes the power over a larger area and/or to multiple focal points on the x-ray anode so that a high dose rate can be achieved. Primarily because of the limitations of the heat load of the x-ray anode, a current state-of-art commercial thermionic x-ray tube can be operated at around 100 kW at an effective focal spot size of 1×1 mm (after reflection). This is insufficient for the dose rate required for MRT. Specifically, previous study of MRT indicates that a dose rate in the order of 100 Gy/sec can be effective, but achieving such dose rates has previously only been possible using a synchrotron source. In the present systems and methods, however, x-ray microbeams MB can be generated around the circumference of a ring- or polygon-shaped anode structure and directed towards target T. By distributing the power over a large area, a much higher x-ray dose can be achieved without generating excessive heat loads at any one x-ray anode. Further, through the use of carbon-nanotube-based field emission x-ray sources 100, the size of the x-ray focal spot can be reduced compared to prior art devices (i.e., less than 1×1 mm).

Further, a system for microbeam radiotherapy can comprise a controller 210 that can set the treatment parameters, including the dose to be delivered, the dwell time, the width of the x-ray radiation plane, and the spacing between adjacent radiation planes. In addition, the system can also comprise a patient bed for supporting the patient undergoing radiotherapy (i.e., object O) and a positioning device 220 that can align target T with the radiation field. For instance, the alignment of x-ray source array 200 can be performed using an x-ray computed tomography (CT) scanner 222 (e.g., a dynamic micro-CT) in connection with positioning device 220. CT scanner 222 can identify the location of target T, as well as any peripheral structures of object O (e.g., normal tissue surrounding a tumor), and positioning device 220 can then be used to align target T with a focus of microbeams MB.

In another aspect of the presently disclosed subject matter, a method for microbeam radiotherapy is provided. The method can comprise positioning distributed x-ray source array 200 about target T to be irradiated (e.g., a tumor within a medical patient), x-ray source array 200 comprising a plurality of carbon-nanotube field emission x-ray sources 100, and simultaneously generating a plurality of x-ray microbeams MB from the plurality of carbon-nanotube field emission x-ray sources 100. X-ray source array 200 can be structured such that x-ray microbeams MB can be generated from the plurality of field emission x-ray sources 100 at different locations on x-ray source array 200. X-ray sources 100 can be switched to deliver x-ray microbeams MB to either one or several parallel radiation planes on target T in a short time. A treatment planning program can be used to determine the radiation dose, the width of the x-ray beam, the spacing between the x-ray radiation planes, and the exposure time, each of which can be controlled by a controller 220 in communication with x-ray source array 200.

To generate multiple and parallel irradiation planes, either object O in which target T is contained or x-ray source array 200 can be translated after each exposure to a sequence of positions within a small interval, and x-ray source array 200 can be operated to irradiate target T after each translation. The process can be repeated until the entire area of target T is irradiated. In this way, x-ray source array 200 can deliver x-ray radiation to target T with the dose being distributed in alternating high and low dose planes.

Figure 9:
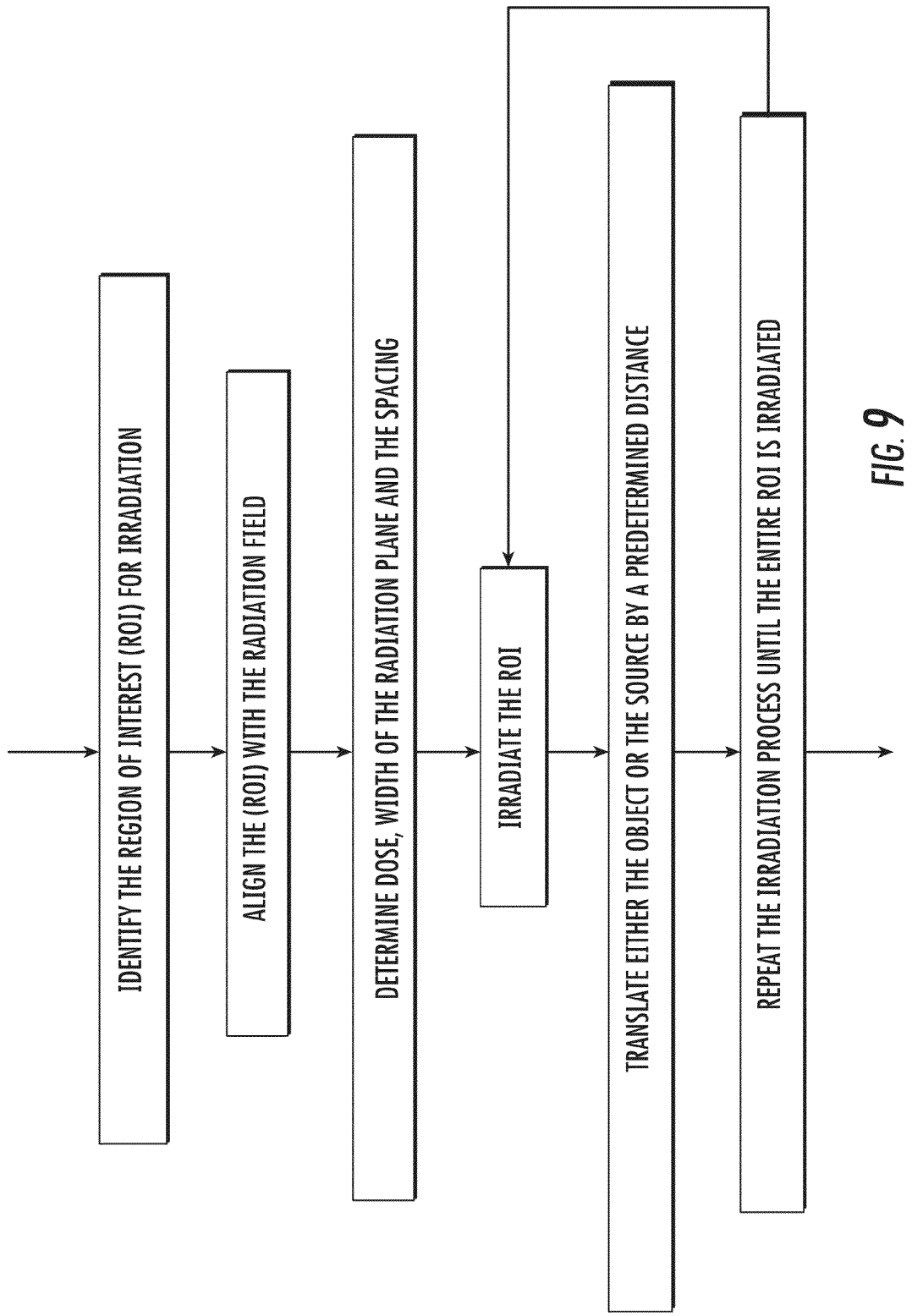
FIG. 9 is a flow chart for a method for microbeam radiotherapy according to an embodiment of the presently disclosed subject matter.

The steps for an exemplary process according to this method are shown in FIG. 9. Specifically, a method for microbeam radiotherapy can comprise identifying a region of interest (ROI) for irradiation (e.g., target T), and aligning the ROI with a radiation field. For instance, aligning the ROI can comprise positioning object O on a patient bed and aligning the region of interest of object O to be irradiated, such as a tumor (i.e., target T), with a focus of x-ray microbeams MB. For example, a positioning device 220 discussed above can be used to align target T with the radiation field. This alignment can be facilitated by first locating target T within object O. As discussed above, this locating can be accomplished using an imaging device, such as an x-ray computed tomography scanner 222. It can be further advantageous to monitor the location of target T during the course of treatment. For example, physiological motions of object O generally or target T specifically can be monitored, and the operation of x-ray source array 200 can be synchronized with such physiological motions, which can minimize blurring of the irradiation field due to the motions. Once the ROI has been aligned, the method can further comprise determining a dose, width, and spacing of the radiation plane generated by x-ray source array 200, and irradiating the ROI. As discussed above, either object O or x-ray source array 200 can be translated by a predetermined distance, and the irradiation process can be repeated until the entire ROI is irradiated.

In summary, compact systems and methods are disclosed that can generate spatially discrete x-ray microbeams with planar and other geometries with high dose rate for microbeam therapy. Such microbeam radiotherapy systems and methods can provide can be used for human cancer treatment such as human external beam treatment, intra-operative radiation therapy, brachytherapy, and for preclinical cancer research on animal cancer models.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

What is claimed is:

1. A method for image guided microbeam radiation therapy, comprising:
   imaging a patient to identify a treatment region;
   positioning the patient in a microbeam irradiator, wherein the irradiator comprises a plurality of distributed x-ray source arrays, wherein each of the plurality of distributed x-ray source arrays comprises one or more elongated focal tracks on a respective x-ray anode, and one or more of a microbeam collimator and a conformal collimator;
   aligning the treatment region with a microbeam irradiator position; and
   irradiating the treatment region with a plurality of microbeam arrays simultaneously from a plurality of entrance angles with prescribed beam energy, width, pitch, dose, and peak-to-valley-dose-ratio.

2. The method of claim 1, further comprising synchronizing or gating x-ray microbeam radiation delivery with physiological motions to reduce motion induced microbeam dosimetry blurring.

3. The method of claim 1, further comprising translating the patient or the microbeam irradiator by a predetermined interval after each microbeam irradiation and repeating the process until an entire treatment region is treated by the prescribed beam energy microbeam irradiation.

4. The method of claim 1, wherein the plurality of the x-ray source arrays are configured to deliver an interfaced microbeam radiation pattern in the treatment region to increase valley dose for better tumor control while keeping the valley dose below a threshold value for normal tissue sparing outside the treatment region.

5. A compact microbeam radiotherapy system comprising:
   a distributed x-ray source array positioned to surround an object to be irradiated and produce x-ray radiation that directs towards a common treatment volume;
   a microbeam collimator positioned between the x-ray source array and the object to be irradiated to collimate the x-ray radiation into either one microbeam or a plurality of substantially parallel microbeams;
   a positioning device for aligning a treatment target of the object with the microbeams; and
   a control system in communication with the x-ray source array for generation of microbeams with pre-determined energy, x-ray dose and dose rate.

6. The system of claim 5, wherein the x-ray source array comprises a field emission x-ray source array.

7. The system of claim 5, wherein a width of each microbeam is less than about 1 millimeter and wherein separation between adjacent microbeams is less than 10 millimeters.

8. The system of claim 5 wherein the x-ray source array comprises multiple and parallel cathode arrays wherein the system is configured such that an electron beam from each cathode array is focused to a narrow line focusing track on an x-ray anode wherein effective width of each line focusing track is similar to a width of the microbeam and effective spacing between the adjacent focusing track is similar to spacing between adjacent microbeams.

9. The system of claim 5 further comprising an x-ray computed tomography imaging system positioned for identifying location of the treatment target.

10. An image guided compact microbeam radiotherapy system comprising:
   a microbeam irradiator comprising a distributed x-ray source array configured to produce x-ray radiation directed towards a common treatment volume, a microbeam collimator to collimate the x-ray radiation into either one microbeam or a plurality of substantially parallel microbeams, and a conformal collimator configured to confine the microbeam radiation to substantially only the treatment volume;
   an imaging device for locating the treatment volume in an object;
   a positioning device for aligning the treatment volume with the microbeam or microbeams;
   a control system in communication with the x-ray source array for generation of microbeams with pre-determined energy, x-ray dose and treatment time; and an electronic control unit that synchronizes delivery of the x-ray radiation with physiological motion of the object to minimize motion induced microbeam beam width blurring.

11. The system of claim 10 wherein the x-ray source array comprises an electron field emission x-ray source array configured for synchronizing radiation delivery with physiological motion of the object by regulating extraction voltage with physiological signals including cardiac and respiratory signals of the object under treatment.

12. An image guided compact microbeam radiotherapy system comprising:
- a microbeam irradiator comprising a plurality of distributed x-ray source arrays each configured to produce a plurality of parallel and conformal microbeams directed toward a common treatment volume, wherein the microbeams generated from each x-ray source array are substantially parallel to each other and are interlaced at a treatment volume such that a high energy density is deposited at the treatment volume compared to the surrounding areas;
- an imaging device for locating the treatment volume in the object;
- a positioning device for aligning the treatment volume with the microbeams; and
- a control system in communication with the x-ray source array for generation of microbeams with pre-determined energy, x-ray dose and treatment time.

* * * * *

UNITED STATES PATENT AND TRADEMARK OFFICE
CERTIFICATE OF CORRECTION

| | | |
|---|---|---|
| PATENT NO. | : 8,995,608 B2 | Page 1 of 1 |
| APPLICATION NO. | : 14/090863 | |
| DATED | : March 31, 2015 | |
| INVENTOR(S) | : Zhou et al. | |

It is certified that error appears in the above-identified patent and that said Letters Patent is hereby corrected as shown below:

In the Specification

At column 1, beginning at line 18 under the title "GOVERNMENT INTEREST" replace the paragraph therein with the following paragraph:

-- This invention was made with government support under Grant Nos. CA119342 and CA118351 awarded by the National Institutes of Health. The government has certain rights in the invention. --

Signed and Sealed this
Twenty-first Day of July, 2015

Michelle K. Lee
*Director of the United States Patent and Trademark Office*